United States Patent [19]

Cheney et al.

[11] Patent Number: 5,441,671
[45] Date of Patent: Aug. 15, 1995

[54] SKIN CLEANSING COMPOSITION

[75] Inventors: Michael Cheney, Fairfield; Donald Feliciano, Milford; Susan Wivell, Madison, all of Conn.

[73] Assignee: Chesebrough-Pond's USA Co., Division of Conopco, Inc., Greenwich, Conn.

[21] Appl. No.: 204,687

[22] Filed: Mar. 1, 1994

[51] Int. Cl.$^6$ ................................................ C11D 1/12
[52] U.S. Cl. ................................... 252/549; 252/89.1; 252/174; 252/132; 252/134; 252/557; 252/DIG. 16; 424/70.1
[58] Field of Search ............... 252/174, 132, DIG. 16, 252/89.1, 549, 554, 555, 557, 551, 174.16, 545, 546; 424/70

[56] References Cited

U.S. PATENT DOCUMENTS

| | | | |
|---|---|---|---|
| 2,894,912 | 7/1959 | Geitz | 252/121 |
| 3,728,447 | 4/1973 | Osipow et al. | 424/70 |
| 3,879,309 | 4/1975 | Gatti et al. | 252/121 |
| 3,951,842 | 4/1976 | Prince et al. | 252/117 |
| 4,180,470 | 12/1979 | Tokosh et al. | 252/121 |
| 4,198,311 | 4/1980 | France et al. | 252/117 |
| 4,260,507 | 4/1981 | Barrett | 252/121 |
| 4,673,525 | 6/1987 | Small et al. | 252/132 |
| 4,695,395 | 9/1987 | Caswell et al. | 252/121 |
| 5,139,781 | 8/1992 | Birwistle et al. | 424/401 |
| 5,262,079 | 11/1993 | Kacher et al. | 252/112 |

Primary Examiner—Paul Lieberman
Assistant Examiner—Necholus Ogden
Attorney, Agent, or Firm—Milton L. Honig

[57] ABSTRACT

A cleansing composition in toilet bar form is described which includes an acyl isethionate salt as surfactant and a behenyl lactylate salt as a firmness additive. Additionally, the composition may contain a moisturizer cocktail of mineral oil, glycerin and silicone oil. Toilet bars herein described have improved mush and wear properties.

10 Claims, No Drawings

SKIN CLEANSING COMPOSITION

BACKGROUND OF THE INVENTION

1. Field of the Invention

The invention relates to a skin cleansing composition containing acyl isethionate as surfactant, especially a composition in the form of a toilet bar.

2. The Related Art

Every day all of us wash our hands, and usually with the aid of a cleansing composition. This frequency of use places important demands on the cleanser. Simply delivering a cleansing effect is insufficient. Compositions must be skin friendly, causing little or no irritation, must allow retention of natural dermal oils and must avoid a dry feeling that would leave skin unpleasantly taut. Traditional soaps, i.e. alkalimetal fatty acids, fail in meeting these criteria.

Synthetic detergents are well known and have achieved increasing popularity. Selected types of synthetic detergents have proved much milder than soap but have failed in other properties. Sometimes lathering characteristics are poor. When in the form of a toilet bar, the more popular mild synthetic detergents exhibit such undesirable properties as bar softening leading to mush and excessive wear rates. Manufacturing difficulties are often also found with bars based on synthetic detergents.

Acyl isethionates have risen to a preeminent position among synthetic detergents within the toilet bar category. Dove ® and Caress ® have achieved market leadership in the USA beauty bar category mainly because their major ingredient, sodium cocoyl isethionate, is much milder than soap and provides an exceptional lather. These characteristics have been described in U.S. Pat. Nos. 2,894,912 (Geitz), 3,879,309 (Gatti et al.), 3,951,842 (Prince et al.), 4,180,470 (Tokosh et al.) and 4,260,507 (Barrett) all assigned to Lever Brothers Company and suggesting solutions to improve the aforementioned problems. In U.S. Pat. No. 4,198,311 (France et al.) sodium cocoyl isethionate toilet bars have been improved through the use of at least 1% sodium isostearyl lactylate to achieve such skin conditioning properties as non-oiliness, silkiness, smoothness and non-powdery feel following rinsing and drying.

Improvements in bar firmness through use of additives such as behenic acid have been reported in U.S. Pat. No. 5,262,079 (Kacher et al.).

Reduction of mush/wear has been obtained through combination of acyl isethionate with a major amount of soap. Mildness is only slightly compromised while mush/wear properties dramatically improve. Lever 2000 ®, a commercially successful deodorant bar in the USA, is based on the aforementioned technology more fully described in U.S. Pat. No. 4,695,395 (Caswell et al.).

Acyl isethionates are mild surfactants, as previously noted. Certain types of additives have been reported which boost mildness into the so-called ultra range. For instance, U.S. Pat. No. 4,673,525 (Small et al.) incorporates moisturizers such as certain sodium acyl lactylates, and polymeric skin feel aids such as cationic polymers. Incorporation of these additives can often adversely affect bar firmness. It would be desirable to obtain a toilet bar based upon acyl isethionate surfactants which exhibits the highest level of mildness while not compromising firmness.

Accordingly, it is an object of the present invention to provide a toilet bar whose major surfactant is acyl isethionate and is ultra mild to the skin.

Another object of the present invention is to provide a toilet bar whose major surfactant is acyl isethionate and exhibits improved firmness with less mush and lower wear rates.

A still further object of the present invention is to provide a toilet bar whose major surfactant is acyl isethionate and exhibits improved moisturization and lathering properties.

These and other objects of the present invention will become more readily apparent upon review of the summary, detailed description and examples which follow.

SUMMARY OF THE INVENTION

A cleansing composition is provided which includes:
(i) from about 0.01 to 0.8% by weight of a behenyl lactylate salt; and
(ii) from about 10% to 90% by weight of a $C_8$–$C_{22}$ acyl isethionate.

Behenyl lactylate salt is present in the compositions to improve mildness, moisturization, antimicrobial activity and, most importantly, provide firmness to toilet bars containing acyl isethionate. Advantageously, the compositions may further be improved through incorporation of small amounts of silicone oil, glycerin and mineral oil.

DETAILED DESCRIPTION OF THE INVENTION

Now it has been found that behenyl lactylate salts improve toilet bar properties of systems containing acyl isethionate. Accordingly, compositions of the present invention will include from about 0.01 to 0.8%, preferably from about 0.1 to 0.6%, optimally from about 0.2 to 0.4% by weight of behenyl lactylate salt. The preferred salts are the alkalimetal, alkaline earth metal, ammonium and $C_2$–$C_{12}$ alkanolammonium salts. Most preferred is sodium behenyl lactylate. This material is commercially available from the C.J. Patterson division of RITA Corporation.

While behenyl lactylate salts are essential, lower molecular weight lactylates including the $C_6$–$C_{18}$ acyl lactylate salts may also be useful. For instance, sodium lauryl lactylate may be present in amounts ranging from about 0.01 to about 0.8%, preferably from about 0.1 to 0.6%, optimally from about 0.2 to 0.4% by weight. Particularly effective is a combination of behenyl and lauryl lactylate salts in a ratio ranging from about 10:1 to 1:10, preferably from about 2:1 to about 1:2, optimally about 1:1 by weight.

Acyl isethionates are the second critical element of compositions according to the present invention. The acyl isethionate can be defined by the following general formula:

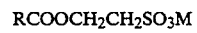

$$RCOOCH_2CH_2SO_3M$$

wherein R is an aliphatic radical or mixture of aliphatic radicals having from 6 to 22 carbon atoms, and M is an alkalimetal cation, such as sodium, potassium, ammonium or $C_2$–$C_{10}$ alkanolammonium cation. In one embodiment according to the present invention, at least 75% of the R radicals should have from 12 to 18 carbon atoms and up to 25% should have from 8 to 10 carbon atoms. Sodium salts are somewhat less water soluble than the potassium salts, and give a firmer bar. Potassium salts produce bars having better lathering properties and a better feel, but are more difficult to process.

Acyl isethionates will generally be the major surfactant present in a range from about 10 to 90%, preferably from about 30 to 80%, optimally between about 45 and 65% by weight of the composition.

Supplemental surfactants for boosting lather may also be incorporated into compositions according to the present invention. Soaps are particularly suitable for this purpose. The term "soap" is used herein in its popular sense, i.e., the alkalimetal or alkanolammonium salt of an alkane- or alkene monocarboxylic acid. Sodium soaps are most preferred. The chain length of the monocarboxylic acids can range from about 12 to 22 carbon atoms, preferably about 12 to about 18 carbon atoms. Most effective are soaps having a fatty acid distribution of about 85% coconut oil and about 15% tallow, most especially an 82:18 mixture, respectively.

Amounts of soap may range from about 1 to about 15%, preferably from about 5 to about 15%, optimally from about 9 to about 13% by weight.

Other synthetic detergents may also be used as supplemental lather boosters. These detergents may be chosen from the alkalimetal, alkaline earth metal or ammonium salts of the following materials:

$C_{12}$–$C_{16}$ hydroxyalkane sulfonates,
$C_8$–$C_{18}$ acyl taurinates,
$C_{12}$–$C_{18}$ alkyl sulfates,
$C_{12}$–$C_{18}$ alkyl ether sulfates,
$C_{12}$–$C_{16}$ alkyl phosphonates and phosphates,
$C_{12}$–$C_{16}$ mono-alkyl succinates and maleates,
$C_6$–$C_{14}$ dialkylsulfosuccinates,
$C_{16}$–$C_{20}$ alkane disulfonates, and
$C_8$–$C_{18}$ alkene sulfonates.

Amounts of the supplemental synthetic detergent may range from about 0.5 to about 20%, preferably from about 1 to about 5% by weight.

Free fatty acids of 8-22 carbon atoms are desirably incorporated within compositions of the present invention. Some of these fatty acids are present to operate as superfatting agents and others as skin feel and creaminess enhancers. Superfatting agents enhance lathering properties and may be selected from fatty acids of carbon atoms numbering 8-18, preferably 10-16, in an amount up to 25% by weight of the composition. Skin feel and creaminess enhancers, the most important of which is stearic acid, are also desirably present in these compositions. Amounts of the free fatty acids may range from about 5 to about 25%, preferably from about 10 to about 20%, optimally between about 16 and about 19% by weight.

Electrolytes in the form of inorganic salts may be included in compositions according to the present invention. These electrolytes are present to assist in reducing plasticity, mush and wear. Useful for this purpose are sodium sulfate, sodium chloride and mixtures thereof. Amounts of each of these materials may range from about 2 to about 10%, preferably from about 4 to about 8% by weight.

Moisturizing agents may be incorporated into compositions of the present invention. Particularly suitable for this purpose is a combination of glycerin, mineral oil and a silicone oil (especially dimethicone). Amounts of glycerin may range from about 0.1 to about 5%, preferably from about 0.5 to about 2%, optimally from about 0.6 to about 1.2% by weight. Mineral oil may be present from about 0.1 to about 2%, preferably from about 0.05 to about 0.5%, optimally from about 0.1 to about 0.3% by weight. Silicone oil may be present from about 0.1 to about 0.5%, preferably from about 0.02 to about 0.1% by weight. Total amount of moisturizer in the form of glycerin, mineral oil and silicone will range from about 0.2 to about 2%, preferably from about 0.8% to about 1.5%, optimally about 1% by weight.

Water will also be present in compositions according to the present invention. Amounts of water will range from about 1 to about 10%, preferably from about 2 to about 8%, optimally between about 3 and about 6% by weight.

Minor functional ingredients may also be included in compositions according to the present invention. These may include opacifiers such as titanium dioxide present at levels from about 0.1 to about 0.5% by weight, germicides such as 2,4,4'-trichloro- 2'-hydroxy diphenyl ether (available as Irgasan DP-300 ®) present from about 0.5 to about 2% by weight, perfumes present from about 0.5 to about 1.5% by weight and colorants present in an effective amount to provide a desired color.

The following examples will more fully illustrate the embodiments of this invention. All parts, percentages and proportions referred to herein and in the appended claims are by weight of the total composition unless otherwise stated.

EXAMPLE 1

The following compositions are illustrative of the present invention.

| COMPONENT | FORMULA WEIGHT % | | | | | |
|---|---|---|---|---|---|---|
| | 1 | 2 | 3 | 4 | 5 | 6 |
| Sodium Cocoyl Isethionate | 44 | 45 | 50 | 44 | 44 | 60 |
| Stearic Acid | 19 | 17 | 15 | 19 | 19 | 15 |
| Sodium Tallowate/Cocoate | 7 | 7 | 7 | 8 | 8 | 7 |
| Sodium Isethionate | 2 | 2 | 2 | 2 | 2 | 2 |
| Sodium Alkylbenzene-sulfonate | 2 | 2 | 2 | — | 2 | — |
| Sodium Sulfate | 5 | 5 | 5 | 5 | 5 | 5 |
| Sodium Chloride | 5 | 5 | 5 | 5 | 5 | 5 |
| Fragrance | 1 | 1 | 1 | 1 | 1 | 1 |
| Titanium Dioxide | 0.2 | 0.2 | 0.2 | 0.2 | 0.2 | 0.2 |
| 2,4,4'-Trichloro-2'-hydroxy Diphenyl Ether | — | — | — | 0.3 | 0.3 | 0.3 |
| Sodium Behenyl Lactylate | 0.3 | 0.5 | 0.3 | 1.0 | 0.3 | 0.3 |
| Sodium Lauryl Lactylate | 0.3 | 0.1 | 0.3 | 0.5 | 0.3 | 0.3 |
| Mineral Oil | 0.2 | 0.2 | 0.2 | — | — | — |
| Glycerin | 0.8 | 0.8 | 0.8 | — | — | — |
| Dimethicone | 0.1 | 0.1 | 0.1 | — | — | — |
| Water | qs | qs | qs | qs | qs | qs |

EXAMPLE 2

Clinical efficacy of compositions according to the present invention were evaluated through an In-Shower Washing Study. The study involved handwashing each bar (n=5 bars/type) continuously in a steamy shower (35°-41° C.) for 1.5 minutes (timed). Excess water was shaken off twice and the bar replaced in the soapdish. Bars were then left to dry overnight. In the morning, the washing procedure was repeated. After three hours, washing was again repeated. Bars were then left to dry over a second night. In the morning, the bars were turned over and the area of the mushy spot was measured ($mm^2$). The percent mush surface area was calculated as follows:

Mush Areas as Percent of Bar Size ($\times$ 100) =

-continued $$\frac{\text{length} \times \text{width of mush spot}}{\text{length} \times \text{width of bar}}$$

Three toilet bars were evaluated. The first bar designated "D" was according to Formula I outlined under Example 1, but absent the lactylates, mineral oil, glycerin and dimethicone. The second test bar designated "DV" was identical in composition to that of "D" but also included a moisturizer cocktail (mineral oil/glycerin/dimethicone). The final bar designated "DVAL" was identical to bar "DV" with a further inclusion of 0.25% sodium lauryl lactylate and 0.25% sodium behenyl lactylate. Mush results are reported in the Table appearing below.

| | MUSH SURFACE AREA ($mm^2$ UNITS) % | |
|---|---|---|
| TOILET BAR # | TEST 1 | TEST 2 |
| D | — | 35.83 |
| DV | 39.97 | 41.78 |
| DVAL | 35.07 | 33.55 |

Lower values for percent mush are more desirable. From the Table it can be seen that bar DVAL provided better results (considerably less mush) than the control bars D and DV. Differences in the values between bars DV and DVAL reported in the Table are statistically significant.

EXAMPLE 3

A consumer panel test was conducted to evaluate various aesthetic properties of the toilet bars designated as D, DV and DVAL (as described in Example 2). In this test, 18 women panelists selected for their previous use of beauty bars, were asked to evaluate the test bars (blind and coded) for one week to replace their regular product. After evaluation, a questionnaire was filled out. Bars were evaluated monadically and rated on a "none to very" scale for each attribute. Results are recorded in the Table below.

| BAR | RATING |
|---|---|
| BAR HARDNESS | |
| D | 0.0 |
| DV | 0.6 |
| DVAL | 19.7 |
| MAINTAINS SHAPE | |
| D | 0.0 |
| DV | 2.3 |
| DVAL | 11.1 |
| MESSY TO USE | |
| D | 0.0 |
| DV | −12.3 |
| DVAL | −15.1 |
| SKIN FEELS SOFT/SMOOTH | |
| D | 0.0 |
| DV | −0.8 |
| DVAL | 12.4 |
| SKIN FEELS COMFORTABLE | |
| D | 0.0 |
| DV | −0.9 |
| DVAL | 12.0 |
| MOISTURIZES SKIN | |
| D | 0.0 |
| DV | 3.4 |
| DVAL | 8.8 |

In each of the above Tables, the higher number is better, except for the Messy To Use category. A clear winner in all of the above tests was that of the DVAL bar.

The foregoing description and examples illustrate selected embodiments of the present invention and in light thereof various modifications will be suggested to those skilled in the art, all of which are within the spirit and purview of this invention.

What is claimed is:

1. A toilet bar composition comprising:
   (i) from about 0.01 to 0.8% by weight of a behenyl lactylate salt; and
   (ii) from about 10% to 90% by weight of a $C_8$–$C_{12}$ acyl isethionate,
   wherein the composition exhibits improved firmness with less mush and lower wear rates.

2. A composition according to claim 1 wherein the acyl isethionate is sodium cocoyl isethionate.

3. A composition according to claim 1 further comprising a $C_6$–$C_{18}$ acyl lactylate salt in an amount from about 0.01 to 0.8% by weight.

4. A composition according to claim 3 wherein said $C_6$–$C_{18}$ acyl lactylate salt is sodium lauryl lactylate.

5. A composition according to claim 4 wherein the ratio of behenyl lactylate salt to sodium lauryl lactylate ranges from about 10:1 to about 1:10.

6. A composition according to claim 5 wherein the ratio of behenyl lactylate salt to sodium lauryl lactylate ranges from about 2:1 to 1:2.

7. A composition according to claim 1 further comprising from about 0.1 to about 10% by weight of a moisturizer.

8. A composition according to claim 7 wherein said moisturizer comprises from about 0.1 to about 2% of mineral oil, from about 0.1 to about 5% of glycerin and from about 0.1 to about 0.5% of silicone oil.

9. A composition according to claim 8 wherein glycerin and silicone oil are present in a respective weight ratio ranging from about 50:1 to about 10:1 and glycerin to a combination of silicone oil and mineral oil are present in a respective weight ratio ranging from about 20:1 to about 1:1.

10. A composition according to claim 3 wherein the behenyl lactylate salt is present from about 0.1 to 0.4% by weight and the $C_6$–$C_{18}$ acyl lactylate salt is lauryl lactylate present from about 0.1 to 0.4% by weight.

* * * * *